(12) United States Patent
Wardlaw

(10) Patent No.: US 8,367,012 B2
(45) Date of Patent: *Feb. 5, 2013

(54) CONTAINER FOR HOLDING BIOLOGIC FLUID FOR ANALYSIS

(75) Inventor: Stephen C. Wardlaw, Lyme, CT (US)

(73) Assignee: Abbott Laboratories, Abbott Park, IL (US)

( * ) Notice: Subject to any disclaimer, the term of this patent is extended or adjusted under 35 U.S.C. 154(b) by 329 days.

This patent is subject to a terminal disclaimer.

(21) Appl. No.: 12/061,394

(22) Filed: Apr. 2, 2008

(65) Prior Publication Data

US 2008/0187466 A1 Aug. 7, 2008

Related U.S. Application Data

(63) Continuation of application No. 10/775,004, filed on Feb. 9, 2004, which is a continuation of application No. 09/256,486, filed on Feb. 23, 1999, now Pat. No. 6,723,290.

(60) Provisional application No. 60/077,214, filed on Mar. 7, 1998.

(51) Int. Cl.
*G01N 21/75* (2006.01)
*B01L 3/00* (2006.01)

(52) U.S. Cl. ...................... 422/401; 422/547

(58) Field of Classification Search .................. 422/401, 422/547
See application file for complete search history.

(56) References Cited

U.S. PATENT DOCUMENTS

| | | | |
|---|---|---|---|
| 3,895,661 A | 7/1975 | Praglin et al. | |
| 3,916,205 A | 10/1975 | Kleinerman | |
| 4,088,448 A | 5/1978 | Lilja et al. | |
| 4,596,035 A | 6/1986 | Gershman et al. | |
| 4,790,640 A | 12/1988 | Nason | |
| 4,902,624 A | 2/1990 | Columbus et al. | |
| 4,950,455 A | 8/1990 | Smith | |
| 5,028,529 A | 7/1991 | Ericcson | |
| 5,132,097 A | 7/1992 | Van Deusen et al. | |
| 5,223,219 A | 6/1993 | Subramanian et al. | |
| 5,275,951 A * | 1/1994 | Chow et al. ..................... | 436/50 |
| 5,281,540 A | 1/1994 | Merkh et al. | |
| 5,316,952 A | 5/1994 | Brimhall | |
| 5,427,959 A * | 6/1995 | Nishimura et al. ........... | 436/534 |
| 5,591,403 A | 1/1997 | Gavin et al. | |
| 5,768,407 A | 6/1998 | Shen et al. | |
| 5,781,303 A * | 7/1998 | Berndt ......................... | 356/632 |
| 5,787,189 A | 7/1998 | Lee et al. | |
| 5,800,781 A | 9/1998 | Gavin et al. | |
| 5,879,628 A | 3/1999 | Ridgeway et al. | |
| 6,127,184 A * | 10/2000 | Wardlaw ........................ | 436/50 |
| 6,358,475 B1 * | 3/2002 | Berndt ......................... | 359/398 |
| 6,387,325 B1 * | 5/2002 | Keusch et al. .................. | 422/50 |
| 6,723,290 B1 * | 4/2004 | Wardlaw ....................... | 422/102 |

FOREIGN PATENT DOCUMENTS

| | | | |
|---|---|---|---|
| EP | 0381501 | 8/1990 | |
| EP | 0638799 | 2/1995 | ........................ 21/5 |
| WO | WO 95/11454 | 4/1995 | ........................ 33/50 |

* cited by examiner

*Primary Examiner* — Lore Jarrett
(74) *Attorney, Agent, or Firm* — O'Shea Getz P.C.

(57) ABSTRACT

A container for holding a biologic fluid sample for analysis is provided which includes a chamber and a label. The chamber includes a first wall, a transparent second wall, and a plurality of features including features spatially located within the chamber. The transparent second wall permits a fluid sample quiescently residing within the chamber to be imaged through the second wall. The plurality of features, including those spatially located within the chamber, are operable to enable the analysis of the biologic fluid. The label directly or indirectly contains information regarding the features and the spatial location of the features within the chamber. The sample is analyzed by an analytical device that utilizes the information communicated through the label.

15 Claims, 5 Drawing Sheets

CONTAINER FOR HOLDING BIOLOGIC FLUID FOR ANALYSIS

This application is a continuation of, and claims priority under 35 U.S.C. §120, U.S. patent application Ser. No. 10/775,004 Feb. 9, 2004 which is a continuation of U.S. patent application Ser. No. 09/256,486 filed Feb. 23, 1999, and claims the benefit of U.S. Provisional Patent application Ser. No. 60/077,214 filed Mar. 7, 1998.

BACKGROUND OF THE INVENTION

1. Technical Field

The present invention relates to apparatus for analyzing biologic fluid samples in general, and to containers for holding a biologic fluid sample during analytical procedures in particular.

2. Background Information

Most analytical methods for evaluating constituents within a biologic fluid sample require that the sample be substantially diluted prior to evaluation. A typical chemical analysis, for example, involves placing a substantially diluted sample into a transparent cuvette of known dimensions and constant light path for evaluation. The cuvette can be made from glass or a hard acrylic that is ground or otherwise manufactured to tight tolerances. The tight tolerances, which are necessary to insure the accuracy of the light path through the cuvette, also make the cuvette undesirably expensive. In hematological analyses, a substantially diluted sample is typically passed through a flow cell within an optical flow cytometer or through an impedance orifice in an impedance type flow cytometer. Most flow cytometers require mechanical subsystems to dilute the sample, to control the sample flow rate through the flow cell, and multiple sensors to evaluate the diluted sample. A special problem associated with hematology measurements is the wide dynamic range of particles that must be enumerated. The red blood cells (RBC's) are the most numerous at about $4.5 \times 10^6$ RBC's per microliter ($\mu$l), followed by the platelets at about $0.25 \times 10^6$ platelets per $\mu$l, and the white blood cells (WBC's) at about $0.05 \times 10^6$ per $\mu$l. Since all cells or particles must be enumerated during a full analysis, the range of cells/particles necessitates at least two dilution levels. The ability to perform multiple dilutions undesirably adds to the complexity of the machine. A person of skill in the art will recognize disadvantages associated with flow cytometers including plumbing leaks and inaccuracies due to fluid control miscalibration. In both of the aforementioned analyses, the operator (or the apparatus itself) must purge the biologic fluid sample from the apparatus and thoroughly clean the apparatus to avoid contaminating subsequent analyses. The substantial dilution required in both analyses also increases the likelihood of error, the complexity of the analysis, and the per analysis cost.

Other analytical methods minimize the above described problems by employing a disposable sample analytical chamber. In one chemical analytical method, the biologic fluid sample is placed in a flexible sealed pouch where it remains during the analysis. This approach avoids the need for plumbing, flow controls, and cleaning the container, but requires a large diluent volume and is restricted to standard measurements of light transmission. In the above method, the light path dimensions are controlled by the analytical instrument, which forms the flexible pouch into a cuvette of the desired thickness at the time of measurement. Other, similar "wet chemical", systems employ a rigid analytical cuvette of specifically manufactured thickness. Other methods for performing a chemical analysis on a biologic fluid sample employ single or multiple test film substrates. The test film substrates also avoid the problems associated with dilution, flow controls, etc., but still require precise sample measurement and placement and are also limited to those analyses that employ light reflectance. The test film substrate methods are further limited by requiring that the associated disposable always have identically located analytical regions; if the desired information is not present in the predetermined analytical areas, then the test film substrate will not yield useful information. Hematological analytical methods which employ a disposable sample analytical chamber include the HemaCue™ and the QBC™. The HemaCue™ system is a method for measuring hemoglobin using a small cuvette. The HemaCue™ method is particularly useful for its intended purpose, but it is unable to measure particulate constituents of whole blood. The QBC™ system, a registered trademark of Becton Dickinson and Company of Franklin Lakes, N.J., USA involves placing a hematological fluid sample within a cylindrical tube and centrifuging the tube and sample for a given period of time. The centrifuge process separates fluid sample constituents into layers according to their density. A float disposed within the tube facilitates evaluation of constituents within each layer. Specific hematological tests may be performed in a disposable test system employing a scannable optical window in a device produced by Biometric Imaging. In this device, a substantially undiluted sample of whole blood is placed into a capillary of known and constant dimension where it is subjected to a laser scan which identifies some sub-types of WBC's. The Biometric Imaging method is also limited in that it is unable to measure any other constituents of whole blood.

Serologic or immunologic analyses measure soluble substances in blood, usually proteins such as specific immunoglobulins. These tests are often performed by admixing the sample with a sensitized particulate, such as latex, which will agglutinate in the presence of the protein of interest. Another method for performing a more quantitative immunological analysis is to use enzymatically linked color changes, such as ELISA. All of these methods are performed on apparatus specialized for their use.

Another common specialized test is urinalysis. The analysis of urine is generally divided into two separate phases: the determination of the bulk and/or chemical properties of the sample and the analysis of particulates within the sample. These analyses require distinctly different disciplines and are usually done separately. There are large and complicated machines that can perform both types of analyses, but they are extremely expensive and require moderate maintenance and operator skill.

None of the above described analytical methods is capable of performing hematological, chemical/immunochemical, and serologic analyses on sample constituents within the same instrument. As a result, it has been necessary to purchase apparatus devoted to performing chemical analyses and apparatus devoted to performing hematological analyses. It has also been necessary to train technicians to operate the various types of apparatus, and to provide laboratory space and maintenance for them. It has also been impossible to combine hematological and chemical analyses in the same apparatus for those analyses where it would be advantageous to combine the analyses. In an analysis to determine anemia, for example, it is preferable to perform both hematological analyses (e.g., hemoglobin, hematocrit, and reticulocyte count) and chemical or immunochemical analyses (e.g., iron or ferritin, and/or vitamin B12 or folate determinations) on the sample. None of the above described methods permit hematological and chemical analyses on a single sample of blood in a single disposable sample chamber. As a result, the laboratory technician must separate and transport the various samples to their separate instruments which are often in separate laboratories, thereby increasing the inefficiency of the process as well as the potential for loss or misidentification of the sample. Also, the results of the analyses may not be available at the same time which increases the difficulty of interpreting the analysis results.

What is needed is a single container for holding a biologic fluid sample that can be used for multiple analyses including but not limited to hematological, chemical, immunological, serological, and urine analyses, one in which multiple analyses can be performed on the same sample in one instrument which presents a common operator interface, one that is operable with substantially undiluted biologic fluid samples, one whose method of sample introduction into the container is similar for each set of analyses, and one that can be used effectively as a disposable.

DISCLOSURE OF THE INVENTION

It is, therefore, an object of the present invention to provide a container for holding a biologic fluid sample which permits analysis of multiple constituents within the same sample, and in particular analysis of constituents residing individually or in groups, using quantitative image analysis.

It is another object of the present invention to provide a container for holding a biologic fluid sample for analysis which is operable for analyses which require information related to the bulk and/or chemical properties of the sample and those which require information related to the particulates content of the sample.

It is another object of the present invention to provide a container for holding a biologic fluid for analysis which is operable in multiple analytical disciplines including but not limited to hematology, chemical/immunochemical, serology/immunological, and urinalysis.

It is another object of the present invention to provide a container which can include analytical chambers of varying dimensions whose thickness can be correlated to a spatial coordinate in order to encompass a wide dynamic range of contained particulates.

It is another object of the present invention to provide a container for holding a biologic fluid sample that requires only a single instrument to sense for information within the sample or associated with the container and interpret the sensed information for use in multiple analyses, thereby decreasing the training and quality control requirements of the laboratory.

It is another object of the present invention to provide a container for holding a biologic fluid sample for analysis that can be used effectively as a disposable.

It is another object of the present invention to provide a container for holding a biologic fluid sample for analysis that does not require substantial dilution of the sample before analysis.

It is another object of the present invention to provide a container for holding a biologic fluid sample which is operable with minimal quantities of blood or other biologic fluid.

It is another object of the present invention to provide a container for holding a biologic fluid sample that facilitates safe handling of the biologic fluid sample for the test operator.

It is another object of the present invention to provide a container for holding a biologic fluid sample that includes an analytical area suitable for imaging by a digital camera or other digital imaging device/image dissector which produces output suitable for quantitative analysis.

It is another object of the present invention to provide a container for holding a biologic fluid sample that has the capability of retaining an untreated or a substantially undiluted sample prior to analysis and releasing said sample into the analytical region when needed.

It is another object of the present invention to provide a container for holding a biologic fluid sample that carries indicia which provides information to the instrument of use in performing the analysis(es) at hand.

According to the present invention, a container for holding a biologic fluid sample for analysis is provided which includes a chamber and a label. The chamber includes a first wall, a transparent second wall, and a plurality of features including features spatially located within the chamber. The transparent second wall permits a fluid sample quiescently residing within the chamber to be imaged through the second wall. The plurality of features, including those spatially located within the chamber, are operable to enable the analysis of the biologic fluid. The features may, for example, include regions where chemical constituents are analyzed, chambers of varying height and size (i.e., physical characteristics) where particulates may be analyzed, and regions, which allow the calibration or quality control of the analysis. The features may also include information that is useful to set-up, adjust, and/or calibrate the analytical device to the task at hand; e.g., filter alignment, lens adjustment, etc. The label directly or indirectly contains information regarding the features and the spatial location of the features within the chamber. The sample is analyzed by an analytical device that utilizes the information communicated through the label.

The preferred analytical device for use with the present invention container is the subject of co-pending U.S. patent application Ser. No. 09/255,673. Briefly described, the "Apparatus for Analyzing Substantially Undiluted Samples of Biologic Fluids" as it is referred to, includes a Reader Module, a Transport Module, and a Programmable Analyzer. The Reader Module includes optics which are operable to image a field within the container, and apparatus to access information through the label attached to the container. The Transport Module includes apparatus for moving the container relative to the Reader Module, or vice versa. The Programmable Analyzer is programmed with instructions to coordinate the operation of the Reader Module and Transport Module according to a variety of analysis algorithms. Which analysis algorithms are used is typically determined by reading the container label.

An advantage of the present invention container is that it is operable for a variety of analyses including but not limited to hematological, chemical, immunochemical, serologic, urinalysis and immunological analyses. In addition, it is possible to perform a multitude of those analyses on the same sample, in the same analytical device. Some traditional analysis methods pass light into a cuvette, and interpret the light traversing through or emitting from the cuvette to provide analytical data. Other methods, such as those which utilize film substrates for analyzing sample constituents utilize light reflected from the film layer. The data available using these types of methods is relatively uniform and does not contain any spatial information. Thus, they are useful for analyzing bulk properties of the sample, meaning those properties that are distributed uniformly in solution or in suspension, but it is impossible to derive useful data about individual particulate materials within the sample. The absence of spatial information limits the number of tests possible on a given sample. If a sample is tested for optical density using the above described cuvette, for example, the test parameters will provide information about a particular constituent, but will not provide the information necessary to characterize cellular contents. The present invention container, in contrast, includes an analytical chamber (or chambers) which includes features that enable the Reader Module to extract both spatial information and quantitative photometric information from the sample quiescently residing within the chamber. The ability to analyze both types of information allows the combination of the instrument and the disposable to analyze a large number of different constituents, and consequently perform a far greater number of tests.

The ability of the present container to include one or more chambers operable for a variety of analyses enables the performance of a select battery of tests on a particular sample. A person of skill in the art will recognize that it is common to perform a battery of tests on a patient sample, and that there is great utility in being able to perform that battery on a single sample in a single analytical device. For example, when a patient's blood sample is being analyzed to determine the hemoglobin concentration, it is usual to measure the hematocrit and white blood count and may be useful to enumerate the reticulocytes. Using the present invention, a chamber having the features of a known or determinable through-plane thickness and appropriate reagents would be used to measure the hemoglobin, and another chamber having the features of a dispersed colorant would be used to measure the hematocrit and white blood count. Another section of that chamber, or a separate chamber, would have the features of a colorant plus a region of very thin through-plane thickness where the reticulocytes would be enumerated. In the case of a battery of tests for the detection of a myocardial infarction, there could be a chamber having features operable to determine treponin and/or myoglobin, a chamber with features for determining potassium concentration, one that analyzed the creatinine phosphokinase levels, etc. An advantage of the present invention is that the chambers and features may be located anywhere within the confines of the container so long as the features are locatable by the analytical device, which allows for a test or series of tests to be designed using the best chamber and feature geometry for the particular analyses on a particular sample without being limited to a chamber region of a predetermined shape or size at a particular location.

The ability to perform different discipline analyses, for example hematological and chemical analyses, is significant for several reasons. First, the amount of equipment required to do the same number of analyses is reduced significantly. It follows that the cost of procuring and maintaining that equipment is similarly reduced. Also, the personnel training required to operate the equipment is reduced. Another reason is the versatility provided by a device that can perform different discipline analyses. Many clinical offices and laboratories are presently unable to justify the office space and expense associated with available test apparatus for each analytical discipline. With the versatile present invention, however, it will be possible to have greater in-house analytical ability because of the present invention's relative minimal space requirements and low cost.

Another advantage of the present invention is that a disposable container for holding, analyzing, and disposing of a biologic fluid sample for analysis is provided. The present invention container is independent of the analytical device, inexpensive, readily loaded, and easily handled by an automated analytical device. The disposable container utilizes a standardized exterior configuration so that the analytical device can be set up for a standard container, regardless of the configuration of the chamber or chambers. In the example above where the container includes one or more chambers having features operable to enable a select battery of tests, the analytical device is set up to accept the standard container and the container label indicates directly or indirectly the tests to be perform and the feature or features within the chamber or chambers that enable those tests. These characteristics make the present container a desirable disposable. As a disposable, the present invention obviates the need to clean the sample chamber after each use and therefore the opportunity for contamination from the prior sample. The disposable nature of the present invention container also facilitates safe handling of the biologic fluid sample for the test operator by minimizing contact with all fluids.

Another advantage of the present invention container is that it uses a relatively small volume of biologic fluid rather than a large volume of significantly diluted biologic fluid. A person of skill in the art will readily recognize the advantages of avoiding the plumbing and fluid controls associated with most flow cytometers which require relatively large volume of diluted sample, as well as the advantages of avoiding the dilution steps, the dilution hardware, and the need for diluent.

Another advantage of the present invention is that it can hold an untreated or substantially undiluted sample prior to analysis and selectively release that sample into the analytical region when needed. As a result, those analyses which are time dependent can be performed using the present invention.

These and other objects, features and advantages of the present invention will become apparent in light of the detailed description of the best mode embodiment thereof, as illustrated in the accompanying drawings.

BEST MODE FOR CARRYING OUT THE PRESENT INVENTION

Figure 1:
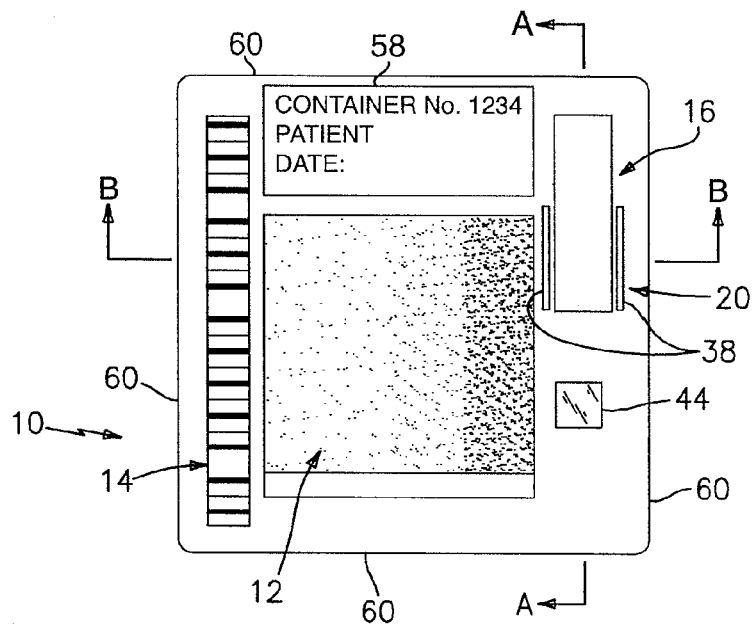
FIG. 1 is a diagrammatic view of the present invention container.
Figure 2:
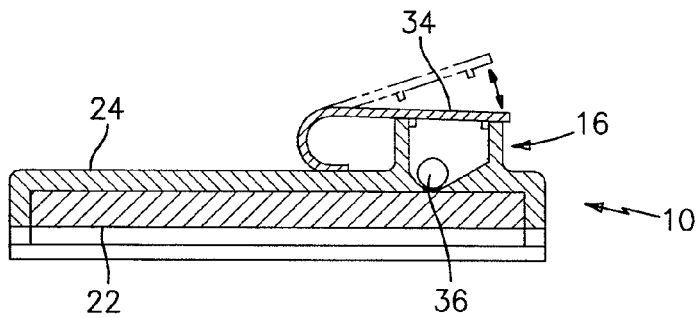
FIG. 2 is a sectional view of the container shown in FIG. 1, sectioned along line A-A.

Referring now to FIGS. 1-4, a container 10 for holding a biologic fluid sample includes at least one chamber 12, a label 14, a reservoir 16, a channel 18, and a valve 20. The container 10 holds a biologic sample in a manner that enables analysis of the sample by an analytical device (not shown) as will be described below. The container 10 embodiment shown in FIGS. 1-4 includes a first piece 22 and a second piece 24 snapped together. The chamber 12 includes a first wall 26 disposed in the first piece 22 and a transparent second wall 28 held between the first piece 22 and second piece 24. An opening 27 disposed within the second piece 24 exposes the transparent second wall 28, and thereby provides visual access into the chamber 12. In some embodiments, the first wall 26 may also be transparent thereby enabling light to pass through the container 10 by way of the chamber 12. The chamber 12 has a through-plane thickness ("t") at any given point. FIG. 6 shows a diagrammatic illustration of a field within a chamber to better illustrate the relationship between volume and through-plane thickness. As used herein, the term "through-plane thickness" refers to a line of sight which corresponds to the shortest distance between the interior chamber surface 30 of the first wall 26 and the interior chamber surface 32 of the second wall 28. The reservoir 16 typically holds 50 µl of biologic fluid sample and preferably includes a cap 34 for sealing the reservoir 16 and a mixing element 36, such as a ball, that operates to keep the sample in uniform suspension. The channel 18 extends between the reservoir 16 and the chamber 12. The valve 20 operates between the reservoir 16 and the chamber 12 to selectively allow passage of fluid from the reservoir 16 to the chamber 12. As used herein, the term "valve" includes not only a structure that includes a movable part that selectively prevents flow, but also any structure that selectively permits flow. The valve 20 shown in FIGS. 1 and 3-5 includes a pair of slits 38 adjacent the reservoir 16 is operated by a rod 40 which is a part of the analytical device. The slits 38 allow the rod 40 to separate the reservoir 16 a small distance from the first piece 22, thereby providing an opening through which biologic fluid can pass through the channel 18 and into the chamber 12. The optimum valve 20 type will vary depending upon the application. In those embodiments where there is more than one chamber 12 (see FIG. 5), each chamber 12 is in communication with the reservoir 16 via a channel 18. The reservoir 16 and valve 20 provide considerable utility for analyses where time is a consideration as will be described below. In some instances, however, it may be advantageous to provide a container 10 without a reservoir 16 and/or a valve 20.

Figure 5:
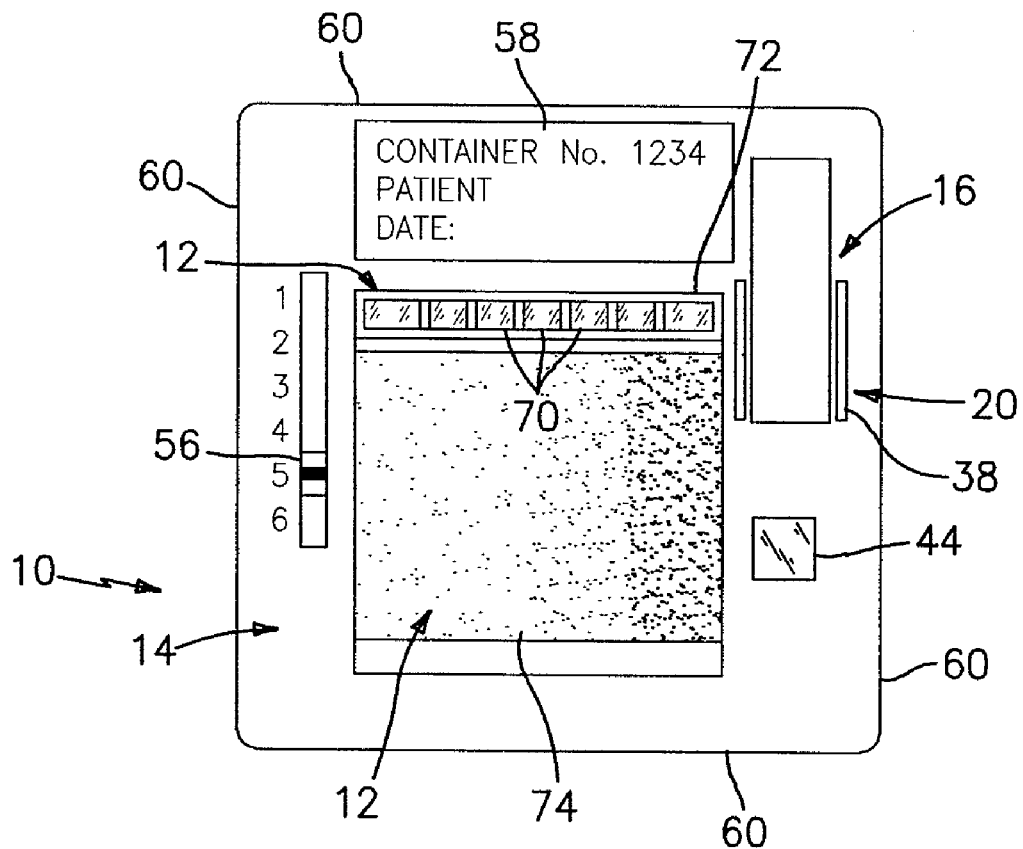
FIG. 5 is a diagrammatic view of a present invention container having two chambers.
Figure 6:
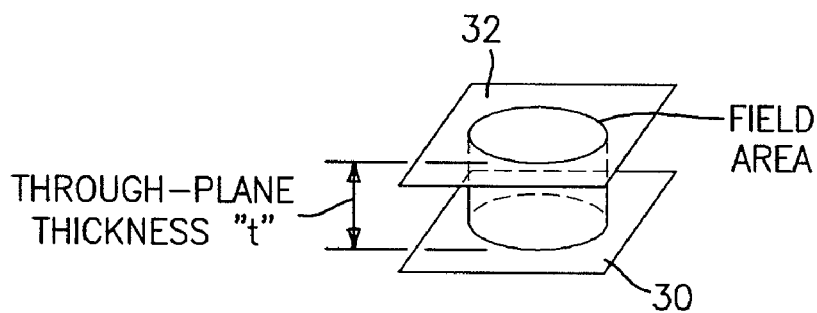
FIG. 6 is a diagrammatic illustration of a field within the chamber.
Figure 7:
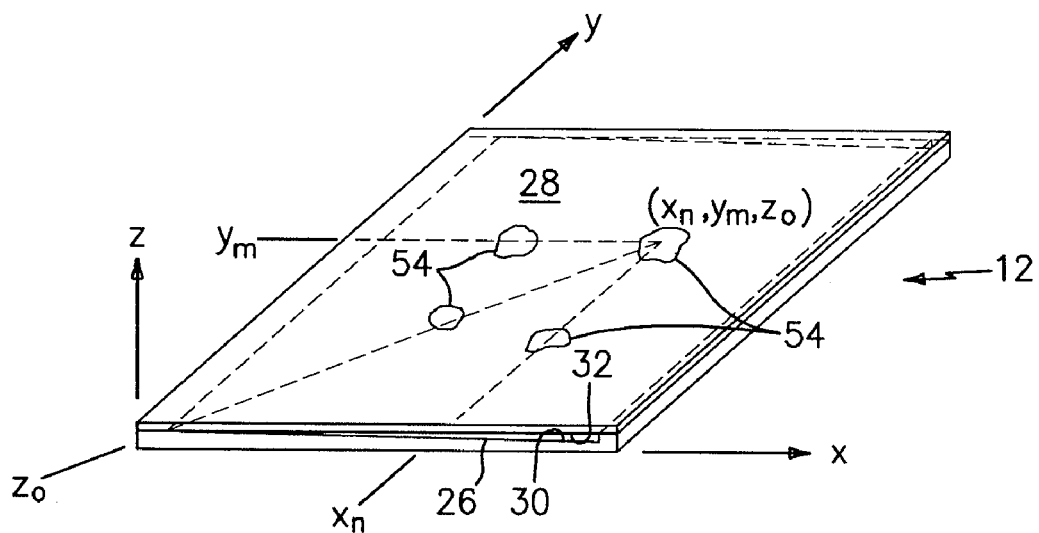
FIG. 7 is a diagrammatic view of a chamber.

Referring to FIGS. 1, 5, and 7, each container 10 includes a plurality of features which are operable to enable the analysis of the biologic fluid sample, some of which are located in the chamber 12. The features located within the chamber 12 are spatially located, each having an address describable, for example, in x,y,z coordinates. The advantage of an x,y,z type coordinate address system is that the chamber can be mapped in an x,y,z, grid with a locatable origin that orients the analytical device relative to the container. The phrase "operable to enable the analysis of the biologic fluid" is used to describe the fact that the features either directly or indirectly provide information that enables the analytical device to provide useful analytical information. To explain further, most analyses require either the volume or the through-plane thickness of the sample be known. The term "volume" as used herein will refer to this requirement since the volume of a given image field of view can be ascertained using the through-plane thickness or vice versa; e.g., when the sample is imaged using a fluorescent light source, it is the volume of the field that provides the useful information directly since fluorescent signal is a function of colorant per unit volume, or when a light absorption technique is used for imaging, the volume of the field indirectly provides the necessary useful information, since absorption is a function of the through-plane thickness of the field (i.e., the distance the light travels through the sample). The through-plane thickness can be readily determined from the sensed volume and the known field area of the analytical device. Features disposed within the chamber can be used to operably enable a means for determining the volume of one or more select fields within the sample.

Figure 3:
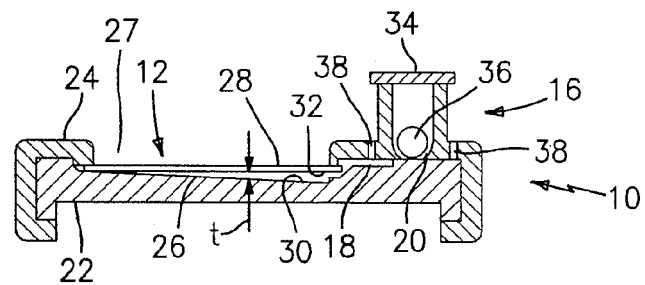
FIG. 3 is a sectional view of the container shown in FIG. 1, sectioned along line B-B.
Figure 4:
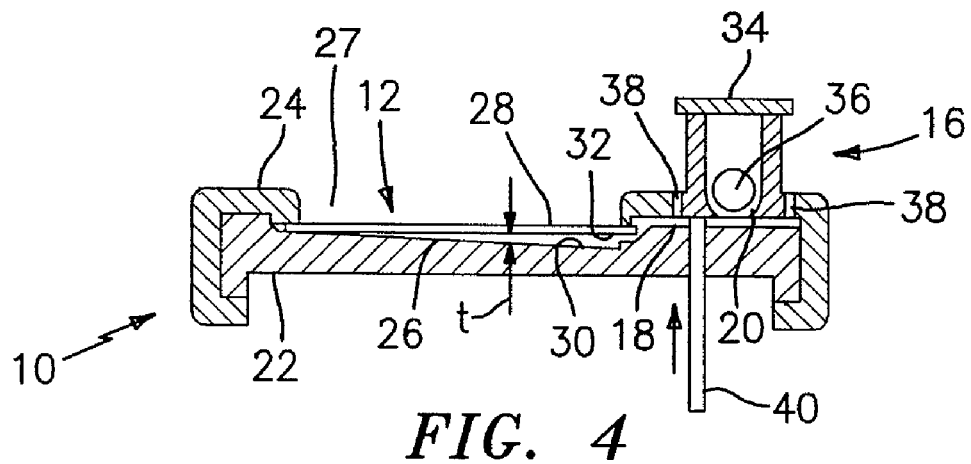
FIG. 4 is the sectional view of FIG. 3, showing the valve actuated open.

Referring to FIGS. 3, 4, and 7, in a first embodiment of the means for determining the volume of one or more fields within the sample, the first wall 26 and second wall 28 of the chamber 12, or a portion thereof, are in fixed relationship to one another and the slope values for each wall 26,28 and a chamber 12 through-plane thickness are known and are communicated to the analytical device through the label 14 (the label 14 is discussed in detail below). The possible configurations of the walls 26,28 (or a portion of the walls 26,28) include parallel walls (i.e., slope =0) separated by a known amount, and walls 26,28 which are at an angle toward one another (i.e., a slope≠0), separated by a known amount. Hence, in this embodiment features that operate to enable the analysis include a known through-plane thickness at one or more known locations within the chamber, particularly when different through-plane thickness' are used to facilitate the analysis. In this embodiment, the through-plane-thickness may also be referred to as a type of physical characteristic, and physical characteristics are a type of feature.

A second embodiment of the means for determining the volume of one or more select fields within the sample includes a known quantity of sensible colorant for mixture with a known volume of biologic fluid sample. As used herein, the term colorant is defined as any reagent that produces a sensible signal by fluorescent emission, or by absorption of light at a specific wavelength, that can be quantified by the analytical device. The colorant has a known signal magnitude to colorant concentration ratio that is communicated to the analytical device through the label 14. The colorant concentration is fixed by virtue of a known volume of biologic fluid sample being added to a known quantity of colorant. Alternatively, the signal magnitude to colorant concentration is determinable by comparison with a second known material such as a pad 44 of material (hereinafter referred to as a "calibration pad"—see FIG. 1) with stable characteristics which is referenced by the analytical device and used to calibrate the response of the colorant. If the colorant signal is sensed in a particular field via the analytical device, then the volume of that field can be calculated using the magnitude of the sensed signal and the known concentration of colorant within the sample. Features that are operable to enable analysis of a biologic fluid with this embodiment include chamber regions where particular analyses are best-performed, located at known spatial locations. The chamber 12 regions where an analysis is best performed refers to those chamber regions having physical characteristics such as a particular through-plane thickness that allow for discrimination of particular constituents within the sample. For example, a chamber through-plane thickness of about 25 microns is known to be favorable for the formation of rouleaux and lacunae within a sample of whole blood. The absence of RBC's in the lacunae makes each lacunae a favorable region to accurately sense colorant signal. Hence, the feature of a chamber region(s) having an approximate through-plane thickness at a particular location(s) within the chamber is used by the analytical device to increase its probability of being able to accurately determine the volume of one or more fields in that region, which volume in turn is used directly in the analysis at hand. In the examples hereafter, the significance of accurately knowing the volume of a field within the lacunae of a whole blood sample will be clearly shown. The analytical device contains means for identifying which features, and therefore the information available with those features, should be used in particular analyses.

Referring to FIGS. 1 and 8A-8F, a third embodiment of the means for determining the volume of one or more select fields includes: 1) a quantity of colorant uniformly dispersed within the biologic fluid; 2) one or more geometric characteristics (i.e., a type of feature) within the chamber 12; 3) chamber 12 regions where particular analyses are best performed; and 4) spatial information locating the geometric characteristic(s)

and optimum region(s) for the analytical device. In this embodiment, it is not necessary to know the amount of sensible colorant within the sample, nor the total volume of the sample. Rather, the field volume determination is done on a comparative basis. A field containing no geometric characteristic is sensed and compared against a field containing a known geometric characteristic. Examples of geometric characteristics include, but are not limited to, a step 46 of known height within one or both walls 26,28, a cavity 48 or protuberance 50 of known height or volume in one or both walls, or an object 52 of known volume. The known volume of the object 52, cavity 48, or protuberance 50 (or volume which is determinable from a step of known height and the cross-sectional area of the field which is known to the analytical device) displaces a known volume of sample. Since the signal from the sensible colorant is a function of sample volume, the difference in signal sensed between the two fields is attributable to the sample volume displaced by the geometric characteristic. Hence, a signal to sample volume ratio can be calculated, and applied to the whole field to ascertain the volume of the field. Like the second embodiment of the means for determining the volume of a sample field, the chamber 12 regions where an analysis is best performed refers to chamber regions having physical characteristics that allow for discrimination of particular constituents within the sample. The spatial information locating the geometric characteristic(s) and optimum region(s) for the analytical device also refers to a chamber 12 coordinate system wherein each feature within the chamber 12 has a coordinate address. The analytical device contains means for identifying which features, and the information available with those features, should be used in particular analyses. In this embodiment, the features that are operable to enable the analysis of a biologic fluid sample include the one or more geometric characteristics and chamber regions where particular analyses are best performed, located at known locations within the chamber.

A fourth embodiment of the means for determining the volume of one or more select fields includes a chamber 12 having specular surfaces on which a virtual reflected image may be detected by the analytical device. The specular surfaces are the two wall surfaces 30,32 in contact with the biologic fluid, or the outer surfaces if the wall thicknesses are known. The analytical device detects the virtual reflected image on one of the specular surfaces 30,32 and then refocuses on the virtual reflected image formed on the second surface 32,30. The distance the analytical device's optics must move between the two images is the through-plane thickness of the chamber 12 in the particular field. The label 14 communicates the coordinate addresses of the select fields within the chamber 12 to the analytical device.

Figure 8A:
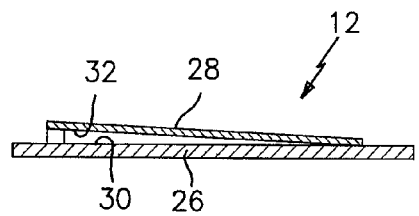
FIGS. 8A-8F are sectioned diagrammatic views of chambers having a variety of features.
Figure 8B:
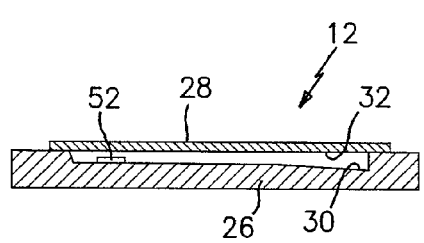
Figure 8C:
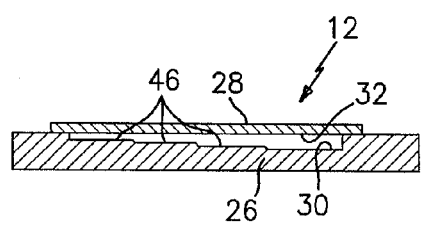
Figure 8D:
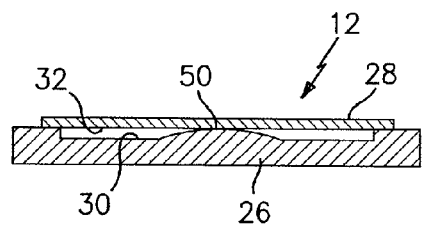
Figure 8E:
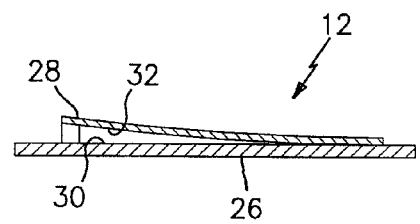
Figure 8F:
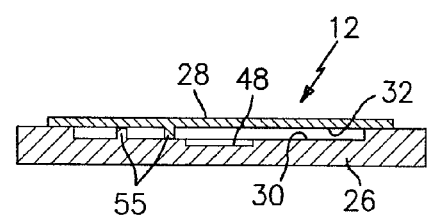

Referring to FIG. 8E, in the second and third embodiments of the means for determining the volume of one or more select fields, one or both of the first or second walls 26,28 may be formed from a flexible material that will deflect a determinable amount due to capillary forces presented by the sample acting on the wall 26,28, and thereby form a desirable convergent relationship between the first wall 26 and the second wall 28.

Referring to FIG. 7, for chemical/immunochemical analyses of a biologic fluid sample, the features operable to enable the analysis of a biologic fluid sample include a plurality of different chemical reagents 54, each located at a particular coordinate address within the chamber 12, and may also include chamber 12 regions where particular analyses are best performed and coordinate addresses locating those optimum regions. In a first embodiment, a known quantity of each chemical reagent 54 is disposed at a particular coordinate address, usually in the form of a coating bound to one of the chamber walls 26,28. When the biologic fluid sample is introduced into the container chamber 12, the biologic sample admixes with each reagent 54. The fluid sample may be contiguous in those regions, but there is no appreciable reagent mixing between adjacent regions for a period of time because of the chamber configuration. Specifically, although the rates of diffusion vertically and laterally are equal, the chamber 12 through-plane thickness (which may be described as a physical characteristic of those regions) is small enough relative to the possible lateral expanse that the chemical reagent 54 will diffuse vertically and reach equilibrium at a much faster rate than it will laterally. In fact, because vertical diffusion reaches equilibrium much faster than lateral diffusion, lateral diffusion may be considered negligible for a short period of time. The lateral spacing between the addresses of the different chemical reagents 54 is such that during that short period of time in which lateral reagent diffusion is negligible, useful analysis of any reaction that may be occurring at a particular address can be performed. The coordinate addresses of the various chemical reagents 54 enable the analytical device to access each reagent 54 and perform meaningful analyses. In those instances where chemical and hematological analyses are desirable, the above described chamber configuration can be provided in a particular region of a single chamber 12 and other configurations provided elsewhere within that chamber 12. The negligible lateral diffusion of the reagent 54 prevents interference with contiguous chamber 12 regions which may be devoted to other type analyses. Alternately, the different reagent regions may be partially or completely isolated in subcompartments of the chamber by means of intervening partitions 55 formed within one or both of the chamber 12 surfaces (see FIG. 8F).

Referring to FIGS. 1 and 5, the label 14 is a mechanism for communicating information to the analytical device. A practical example of a label 14 is one which is machine readable and one which is capable of communicating information including, but not limited to: 1) type of analysis(es) to be performed; 2) information concerning the type of features, and the coordinate addresses of those features located within the sample chamber; 3) reagent information; 4) lot information; 5) calibration data; etc. In one form, the label 14 may be a magnetic strip or a bar code strip, or the like, which directly contains all the information useful to the analytical device in the performance of the analysis(es). This type of label 14 is particularly useful in those instances where the information to be communicated is limited. In those instances where the quantity of information to be communicated is considerable, it may be more desirable to have the label 14 direct the analytical device to a data file (stored within the analytical device or remotely accessible by the analytical device via modem, network link, etc.) containing the appropriate information. In this instance, the label 14 can be said to indirectly contain the information by providing the necessary path to the information. Here again, the label 14 could be a bar code or magnetic strip, which in this case communicates a particular code that is interpreted by the analytical device as being associated with a certain data file. The same result could be achieved by incorporating a physical feature 56 in the container (e.g., a notch, a tab, etc.—see FIG. 5) that is interpretable by the analytical device. Other labels 14 which function to communicate information to the analytical device can be used alternatively.

The container 10 also preferably includes a human readable label 58 to facilitate handling within the laboratory or clinic. The human readable label 58 may include information such as the patient's name, a sample taken date, an office address, an appropriate warning (e.g., "Biohazard—Handle with Care"), trademarks, etc. The sides 60 of the container 10 are suitable to interact with a transport means (not shown) contained within the analytical device. The transport means is operable to move the container 10 relative to an imaging device (not shown) contained within the analytical device.

As stated above, the considerable utility of the container 10 enables a wide variety of analyses to be performed on a single sample, using a single analytical device. The examples given below are offered so that a complete appreciation of the present invention container 10 may be gained.

EXAMPLE I

Hematological Analyses

Referring to FIGS. 1 and 4, to enable an analysis of white blood cells (WBC's) within an anticoagulated whole blood sample, the container 10 includes approximately 0.8 micrograms (μg) of a sensible colorant disposed within the reservoir 16. EDTA is an example of an anticoagulating agent that may be used with the sample and a fluorescent highlighting supravital stain such as acridine orange, basic orange-21, or the like are examples of sensible colorants that may be added to the reservoir 16. For purposes of evaluating WBC's, it is preferable to have a region within the chamber 12 that has a plurality of select fields with a through-plane thickness on the order of 20 microns in magnitude. A chamber 12 through-plane thickness (i.e., a type of physical characteristic) of approximately 20 microns is chosen for a couple of reasons. First, an evaluation volume of 0.02 μl, (formed by a particular field of the chamber 12 having a cross-sectional area of 1 millimeter (mm) and a thickness of 20 microns) typically contains 50-200 WBC's which is a favorable quantity for evaluative purposes. Second, a through-plane thickness of 20 microns provides an optimal chamber 12 for rouleaux and lacunae formation. The coordinate addresses of select fields are communicated to the analytical device by way of the label 14. In the example, therefore, the plurality of features operative to enable analysis of the biologic fluid sample include: 1) the sensible reagent disposed within the reservoir 16; and 2) the chamber 12 region(s) having a plurality of select fields with a particular through-plane thickness, at known coordinate addresses within the chamber 12.

Approximately 20 μl of anticoagulated whole blood is placed into the reservoir 16 by the operator and the cap 34 secured. The container is gently shaken until the reagent and whole blood sample are adequately mixed. A mixing ball 36 disposed in the reservoir 16 facilitates mixing. The container 10 is inserted into the analytical device and the valve 20 is subsequently actuated to release the sample into the chamber 12 by way of the channel 18. Once the sample is distributed within the chamber 12, the sample resides quiescently. The only sample motion within the chamber 12 will possibly be Brownian motion of the sample's formed constituents, and that motion is non-disabling for the present invention. Note that for simple tests such as a WBC count where timing is not important, a sample could be deposited into the chamber 12 directly, thereby obviating the need for a reservoir 16 and valve 20.

Immediately after the sample has been inserted into the chamber, the sample will appear opaque when examined either with transmitted light, or more preferably by epi-illuminated fluorescence. The opaque appearance is caused by the red blood cells (RBC's), which form an overlapping mass prior to the formation of the rouleaux. After lying substantially motionless for approximately thirty (30) seconds, within the chamber 12, the RBC's will have spontaneously clustered into rouleaux, leaving lacunae between the rouleaux. It is in these lacunae where the other whole blood sample constituents (e.g., WBC's and platelets) can be found and evaluated. If a count of WBC's is desired, a square millimeter field of the 20 micron thick chamber 12, which contains 0.02 μl of whole blood sample, can be evaluated. A 0.02 μl sample is chosen to keep the number of WBC's reasonable (a normal whole blood sample contains approximately 7,000 WBC's per μl of sample; a 0.02 μl sample of normal whole blood contains approximately 140 WBC's). A number of these fields would be evaluated until enough cells are counted to get a number which has sufficient statistical accuracy, which is in practice approximately 1000 cells. If additional WBC information is sought, the WBC's (lymphocytes, granulocytes, monocytes, etc.) can be analyzed within the sample using an image dissector such as a CCD camera, for example, alone or with analysis software. A differential count could be determined from the data collected.

The above example of the utility of the present invention container 10 in hematological analyses includes a plurality of features operative to enable analysis of the biologic fluid sample. In a preferred embodiment, the features not only include the plurality of select fields with a through-plane thickness (i.e., a type of physical characteristic) on the order of 20 microns, but fields of slightly larger and smaller volume as well. The larger/smaller field volumes can be created by several of the mechanisms described above; e.g., convergent chamber walls 26,28, or steps 46 within one or both walls 26,28, etc. A range of field volumes is advantageous because constituent populations quite often vary in magnitude within the biologic fluid sample. If, for example, the WBC population within the sample was abnormally high, a chamber 12 region having a through-plane thickness of 20 microns may have more than an optimal number of WBC's for evaluative techniques such as counting. Changing to a field of smaller volume would decrease the number of WBC's and therefore facilitate the analysis at hand. On the other hand, if the WBC population within the sample was abnormally low, a chamber 12 region having a through-plane thickness of 20 microns may have less than an optimal number of WBC's for evaluative purposes. Changing to a field of larger volume would increase the number of WBC's and likewise facilitate the analysis at hand. The spatial locations of alternate features (i.e., larger or smaller through-plane thickness regions in the above example) are communicated to the analytical device through the label 14.

EXAMPLE II

Chemical Analyses

Figure 9:
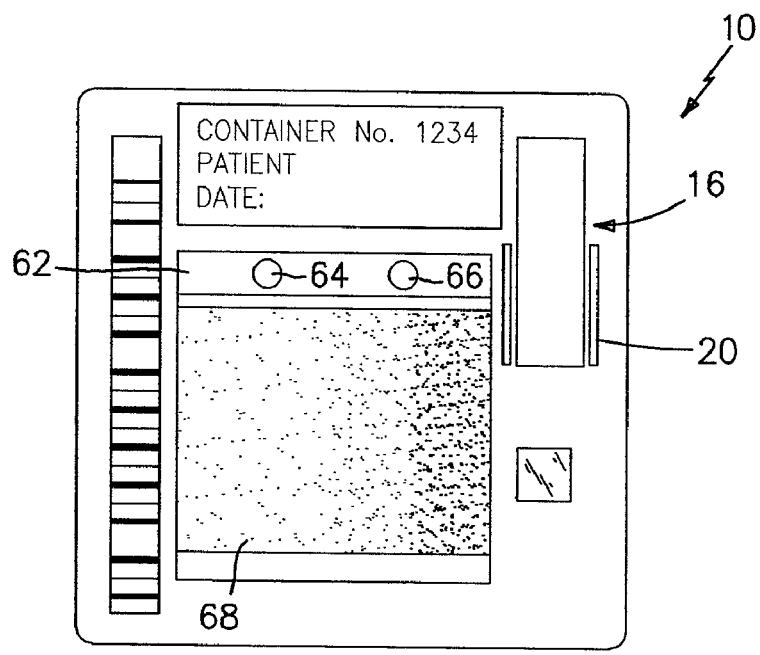
FIG. 9 is a diagrammatic view of a present invention container having two chambers.

Referring to FIG. 9, a complete blood count requires that the RBC's be evaluated for hemoglobin content. In a first embodiment, the hemoglobin evaluation is performed in a first chamber 62 which is connected to the reservoir 16 by a channel 18. At least two chemical reagents 64,66 are initially stored within the first chamber 62. The reagents 64,66 are shown in the first chamber 62 as independent deposits to illustrate the use of multiple reagents. Reagents can often be combined into a single reagent mixture stored as a single deposit. One of the chemical reagents 64 is a lysing reagent which breaks down RBC's within the sample and thereby releases the hemoglobin stored within the RBC's. The other reagent 66 is a hemoglobin stabilizer that increases the reliability of the hemoglobin evaluation. In most cases, the hemoglobin evaluation is performed after the lysing agent has been introduced into the sample for a given period of time, or at particular intervals. Using the present invention, the period of time begins when the valve 20 is actuated to permit the sample to enter the first chamber 62 and a second chamber 68. The remaining analyses associated with a complete blood count are performed in the second chamber 68. In this embodiment, the features operable to enable the analysis of the biologic fluid sample include: 1) the chemical reagents 64,66 disposed in the first chamber 62 at known spatial locations; 2) one or more select fields at know locations where the chemical reagents are disposed; and 3) the valve 20 between the reservoir 16 and the chambers 64,66 that initiates the time period. Additional features such as those described heretofore in the "Hematological Analyses" example may be present in the second chamber 68.

Figure 10:
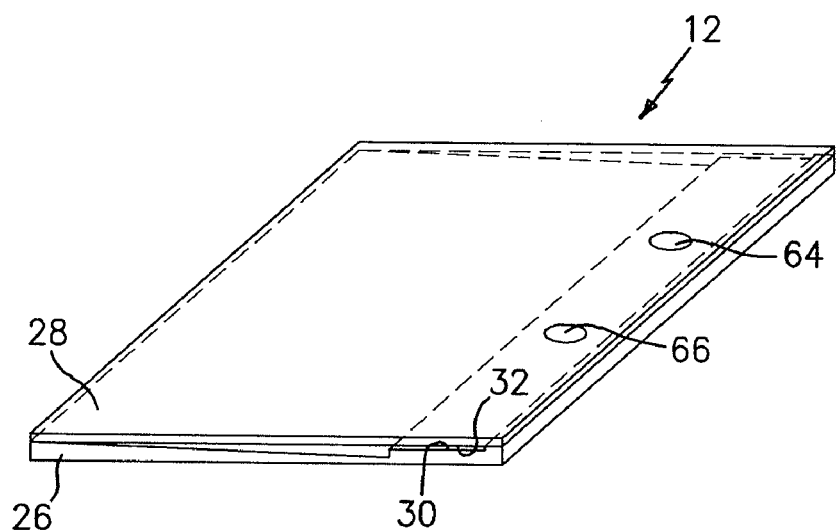
FIG. 10 is a diagrammatic view of a chamber.

Referring to FIG. 10, in a second embodiment all of the complete blood count analyses are performed in a single chamber 12. The portion of the biologic fluid sample used for the hemoglobin evaluation is contiguous with remaining portion of the fluid sample, but that portion is preferably oriented toward one side of the chamber 12 to minimize potential mixing of the lysing agent with the remaining portion of the fluid sample. In addition to orienting the hemaglobin evaluation to one side, it is also preferable to choose a chamber 12 through-plane thickness small enough such that vertical diffusion (and ultimate equilibrium) of the chemical reagents 64,66 within the biologic fluid sample occurs at a much faster rate than lateral diffusion. The difference in diffusion rates is such that lateral diffusion may be considered negligible for a short period of time. The lateral spacing between the hemoglobin evaluation site and the remainder of the fluid sample is such that during that short period of time in which lateral reagent diffusion is negligible, the remainder of the desired analyses can be performed without interference from the lysing agent. In this embodiment, the same two chemical reagents 64,66 as described above are initially deposited in the hemoglobin evaluation region of the chamber 12, and actuating the valve 20 begins the time period for the evaluation. The features operable to enable the analysis of the biologic fluid sample are: 1) the chemical reagents 64,66 disposed in the aforementioned chamber 12 region at known spatial locations; 2) the chamber configuration functionally operable to separate the hemoglobin evaluation region from the remainder of the biologic fluid sample; 3) the valve 20 between the reservoir 16 and the chamber 12 used to initiate the time period; and 4) any features such as those described above in the "Hematological Analyses" example.

EXAMPLE III

Urinalysis

Referring to FIG. 5, a complete urinalysis requires a chemical analysis and a particulate analysis of the urine sample. Chemical reagents 70 spatially located at particular coordinate addresses within a chamber are used to colorometrically relate information after a given period of time. The particulate analysis involves detecting, evaluating and/or enumerating the particles within the sample. In a first embodiment, the chemical analysis is performed in a first chamber 72 and the particulate analysis is performed in a separate second chamber 74. Both the first chamber 72 and the second chamber 74 are in fluid communication with the reservoir 16. In a manner similar to that described above, the through-plane thickness and other physical characteristics of the first chamber 72 and the second chamber 74 are chosen to facilitate the chemical and particulate analyses, respectively. In the first embodiment, the features operable to enable the analysis of the biologic fluid sample are, therefore: 1) the chemical reagents 70 disposed in the first chamber 72 at a known spatial location(s); 2) the physical features at a known spatial location(s) within the chamber 12 chosen to facilitate the chemical analysis; and 3) the valve 20 between the reservoir 16 and the chamber 12 used to initiate the time period. In a second embodiment, the chemical and particulate analyses are performed in the same chamber 12. In a manner similar to the hemoglobin evaluation described above (see FIG. 10), the chamber 12 region devoted to the chemical analysis is preferably oriented to one side of the chamber 12 and the through-plane thickness is such that interference from the chemical reagents will be negligible if at all. The features within the second embodiment operable to enable the analysis of the biologic fluid sample are: 1) the chemical reagents 70 disposed in the chamber 12 at a known spatial location(s); 2) the chamber 12 configuration functionally operable to separate the chemical evaluation region from the remainder of the biologic fluid sample; and 3) the valve 20 between the reservoir 16 and the chamber 12 that initiates the time period.

Although this invention has been shown and described with respect to the detailed embodiments thereof, it will be understood by those skilled in the art that various changes in form and detail thereof may be made without departing from the spirit and the scope of the invention.

I claim:

1. A container for holding a biologic fluid sample for analysis, said container comprising:
    a fluid holding chamber having a first wall and a transparent second wall, and wherein the fluid holding chamber has a mapped interior so that positions within the fluid holding chamber are identifiable by a coordinate address;
    at least one feature operable to enable a determination of the volume of a field of the fluid sample, the at least one feature located within the chamber at a predetermined coordinate address; and
    a label attached to said container, said label including information indicative of the predetermined coordinate address within the fluid holding chamber.

2. The container of claim 1, wherein the interior of the chamber is orthogonally mapped.

3. The container of claim 2, wherein the at least one feature operable to enable a determination of the volume of a field of the fluid sample includes a through-plane thickness, and the field of the fluid sample is located at the predetermined address.

4. The container of claim 2, wherein the at least one feature operable to enable a determination of the volume of a field of the fluid sample includes a geometric characteristic.

5. The container of claim 4, wherein the geometric characteristic comprises a step of known height disposed in one or both of the first wall and second wall.

6. The container of claim 4, wherein the geometric characteristic comprises a cavity of known height or volume disposed in one or both of the first wall and second wall.

7. The container of claim 4, wherein the geometric characteristic comprises a protuberance of known height or volume disposed in one or both of the first wall and second wall.

8. The container of claim 4, wherein the geometric characteristic comprises an object of known volume.

9. A container for holding a biologic fluid sample for analysis, said container comprising:
    a fluid holding chamber having a first wall and a transparent second wall, and wherein the fluid holding chamber has a mapped interior so that positions within the fluid holding chamber are identifiable by a coordinate address;

means for enabling a determination of the volume of a field of the fluid sample, the means located within the chamber at a predetermined coordinate address; and a label attached to said container, said label including information indicative of the predetermined coordinate address within the fluid holding chamber.

10. The container of claim 9, wherein means for enabling a determination of the volume of a field of the fluid sample includes a through-plane thickness, and the field of the fluid sample is located at the predetermined address.

11. The container of claim 9, wherein the means for enabling a determination of the volume of a field of the fluid sample includes a geometric characteristic.

12. The container of claim 11, wherein the geometric characteristic comprises a step of known height disposed in one or both of the first wall and second wall.

13. The container of claim 11, wherein the geometric characteristic comprises a cavity of known height or volume disposed in one or both of the first wall and second wall.

14. The container of claim 11, wherein the geometric characteristic comprises a protuberance of known height or volume disposed in one or both of the first wall and second wall.

15. The container of claim 11, wherein the geometric characteristic comprises an object of known volume.

* * * * *